(12) United States Patent
Arkles et al.

(10) Patent No.: US 8,575,381 B2
(45) Date of Patent: Nov. 5, 2013

(54) TRIHYDRIDOSILYL-TERMINATED POLYSILANES AND METHODS OF PREPARATION

(75) Inventors: Barry C. Arkles, Pipersville, PA (US); Youlin Pan, Langhorne, PA (US); Gerald L. Larson, Newtown, PA (US)

(73) Assignee: Gelest Technologies, Inc., Morrisville, PA (US)

( * ) Notice: Subject to any disclaimer, the term of this patent is extended or adjusted under 35 U.S.C. 154(b) by 241 days.

(21) Appl. No.: 13/234,664

(22) Filed: Sep. 16, 2011

(65) Prior Publication Data

US 2012/0071678 A1 Mar. 22, 2012

Related U.S. Application Data

(60) Provisional application No. 61/383,925, filed on Sep. 17, 2010.

(51) Int. Cl.
*C07F 17/00* (2006.01)
*C07F 7/08* (2006.01)

(52) U.S. Cl.
USPC .......................................... 556/11; 556/430

(58) Field of Classification Search
USPC .................................. 556/11, 430
See application file for complete search history.

(56) References Cited

U.S. PATENT DOCUMENTS 4,079,071 A 3/1978 Neale
5,374,758 A * 12/1994 Mori et al. ............. 556/430
5,942,637 A 8/1999 Boudjouk et al.

OTHER PUBLICATIONS

Jalali-Heravi et al., Chemistry of Materials, vol. 3, No. 6, pp. 1024-1030 (1991).*
Tilley: "Mechanistic Aspects of Transition-Metal Catalyzed Dehydrogenative Silane Coupling Reactions"; Comments Inorg. Chem.; 10(1); pp. 37-51 (1990).
Aitken et al: "Polymerization of Primary Silanes to Linear Polysilanes Catalyzed by Titanocene Derivatives"; J Organometallic Chem., 279, pp. C11-C13 (1985).
Tilley: "The Coordination Polymerization of Silanes to Polysilanes by a "σ-Bond Metathesis" Mechanism. Implications for Linear Chain Growth", Acc. Chem. Res., 26, pp. 22-29 (1993).
Forsyth et al: "Organolanthanide-Catalyzed Dehydrogenative Coupling of Silanes. Mechanistic Implications" Organometallics, 10, pp. 2543-2545 (1991).

* cited by examiner

*Primary Examiner* — Porfirio Nazario Gonzalez
(74) *Attorney, Agent, or Firm* — Panitch Schwarze Belisario & Nadel LLP

(57) ABSTRACT

Novel trihydridosilyl-terminated polysilanes and methods for their synthesis, which are applicable to other polysilanes, are provided. The synthetic methods provide for facile preparation of products with minimal handling of pyrophoric intermediates and byproducts. The novel compounds contain at least three silicon-silicon bonds and at least one terminal silicon atom having three hydrogen substituents.

20 Claims, No Drawings

TRIHYDRIDOSILYL-TERMINATED POLYSILANES AND METHODS OF PREPARATION

CROSS-REFERENCE TO RELATED APPLICATIONS

This application claims the benefit of U.S. provisional patent Application No. 61/383,925, filed on Sep. 17, 2010, the disclosure of which is incorporated herein by reference.

BACKGROUND OF THE INVENTION

Low molecular weight polysilanes having at least one terminating silicon atom bearing three hydrogens are of great interest in the fabrication of electronic devices. The simplest compounds of this class, perhydridopolysilanes, have been known for over a century, having first been disclosed by Alfred Stock. General synthetic methods include hydrolytic decomposition of metal silicides, e.g. magnesium silicide; Wurtz coupling of mixed hydridohalosilanes, e.g. iodosilane; pyrolytic coupling of lower polysilanes, e.g. disilane; reduction of chlorinated polysilanes and polysilane complexes; and dephenylation of perphenylpolysilanes.

Those familiar with the art readily appreciate the difficulty in preparing polysilanes with more than three silicon atoms. For example, synthetic methods generally proceed in relatively low yield and require purification of a pyrophoric mixture of liquid and gaseous products and byproducts. It would be desirable to be able to prepare trihydridosilyl-terminated polysilanes in good yield with minimal handling of pyrophoric intermediates and byproducts.

BRIEF SUMMARY OF THE INVENTION

According to the present invention, trihydridosilyl-terminated polysilanes having formula (1) comprise at least four silicon atoms and at least one silicon terminus bonded to three hydrogen atoms:

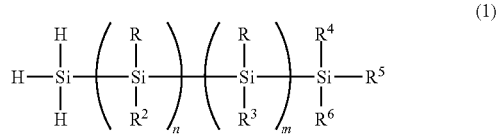

wherein R represents an organic substituent, $R^2$ and $R^3$ are not identical and are independently selected from the group consisting of an organic substituent, a hydrogen, and a substituted silyl group, $R^4$, $R^5$, and $R^6$ are independently selected from the group consisting of an organic substituent, a substituted silicon atom and hydrogen, and m and n are each independently integers selected so that the total number of silicon atoms is at least 4.

A method for preparing a trihydridosilyl-terminated polysilane according to one embodiment of the invention comprises:
(a) preparing a non-pyrophoric aryl-substituted polysilane comprising at least four silicon atoms and an aryl-substituted silicon terminus;
(b) halogenating the aryl-substituted polysilane to produce a halogenated polysilane; and
(c) reducing the halogenated polysilane to yield a trihydridosilyl-terminated polysilane.

A method for preparing a trihydridosilyl-terminated oligodimethylsilane according to another embodiment of the invention comprises:
(a) coupling a halogen-terminated oligosilane with an alkali metal salt of a mono-, di, or tri-aryl silane to form a coupling product;
(b) halogenating the coupling product to form a halogenated intermediate; and
(c) reducing the halogenated intermediate to form a trihydridosilyl-terminated oligodimethylsilane.

DETAILED DESCRIPTION OF THE INVENTION

The present invention is directed to a group of compounds known as trihydridooligosilanes or trihydridosilyl-terminated polysilanes which have the general structure shown in formula (1).

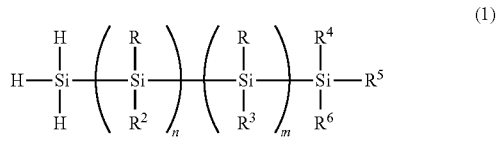

The trihydridooligosilanes contain at least four silicon atoms and preferably contain at least four to about ten silicon atoms. However, there is no upper limit on the number of silicon atoms which may be present. In the compounds according to the invention, at least one terminal silicon atom is bonded to three hydrogen atoms, and the remaining silicon atoms (internal and terminal) have as substituents at least one (and preferably two) organic groups or substituted silicon atoms, with the remaining positions being occupied by hydrogen atoms. In a preferred embodiment, all of the terminal silicon atoms have three hydrogen substituents.

In formula (1), R represents an organic substituent; $R^2$ and $R^3$ are different from each other and are independently selected from the group consisting of an organic substituent, hydrogen or a substituted silyl group; $R^4$, $R^5$, and $R^6$ may be the same or different and are independently selected from the group consisting of an organic substituent, a substituted silicon atom and hydrogen; and m and n are integers independently selected so that the total number of silicon atoms is at least four; either m or n may be 0. Preferably, m and n are selected so that the total number of silicon atoms is between four and about ten. There are no limitations on the organic substituents which may be selected for R, $R^2$, $R^3$, $R^4$, $R^5$, and $R^6$. Appropriate organic substituents may be, without limitation, linear, branched, or cyclic, have any chain length, be unsubstituted or substituted (such as with heteroatoms), may be allyl, alkyl, alkoxy, alkynyl, aryl, aromatic or non-aromatic groups, and may contain larger ring structures (such as ferrocene).

The term "oligosilane" is typically used to describe a polysilane having only a few monomer units. Accordingly, for the purposes of this disclosure, the terms "oligosilane" and "polysilane" are used interchangeably because the polysilanes according to the invention are typically relatively short polymers.

The simplest trihydridosilyl-terminated polysilane according to the invention is 2,2,3,3-tetramethyltetrasilane, having formula (2). This compound is an embodiment of formula (1), wherein m=0, n=2, $R=R^2=CH_3$, and $R^4=R^5=R^6=H$.

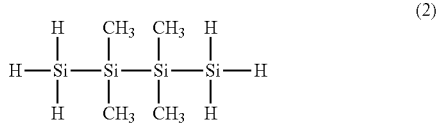

(2)

Other exemplary compounds include trihydridosilyl-terminated permethyloligosilanes, such as shown in formula (3). In this formula, n represents an integer greater than two, preferably between about three and eight.

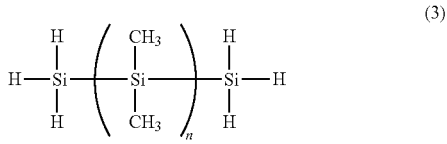

(3)

The backbone of the polysilanes according to the invention may be linear or branched, due to the fact that the internal and terminal silicon atoms in the main chain may be substituted silyl groups. For example, a more complex compound according to the invention is 2-(2-ferrocenylethenyl)isotetrasilane, as shown in formula (4).

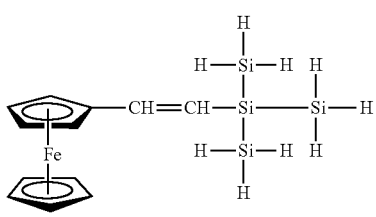

(4)

Method of Synthesis via Aryl-Substituted Polysilane Intermediate

A first method of preparing the trihydridosilyl-terminated polysilanes according to the invention comprises three main steps, which will be described in more detail below. These steps include preparation of an aryl-substituted polysilane, halogenation of the polysilane to produce a halogenated polysilane, and reduction to yield the desired product.

The first step in the method involves preparing a polysilane having at least four silicon atoms. The polysilane contains at least one and as many as three aryl groups on the silicon terminus that will ultimately be converted to a trihydridosilyl terminus. The remaining silicon atoms may be substituted with hydrogen atoms, alkyl (such as the preferred methyl) groups, or aryl groups. In a preferred embodiment, the oligosilane contains no more than five aryl substituents. There is no upper limit on the number of silicon atoms that may be present in the oligosilane; it must be the same as the number of silicon atoms in the desired trihydrido-terminated product. Preferred aryl-substituted oligosilanes contain four to about ten silicon atoms. Exemplary aryl groups include phenyl and substituted aryl groups such as, without limitation, tolyl and anisyl. The aryl substituents on the terminal and internal silicon atoms may be the same or different. In a preferred embodiment, the total number of aryl groups is no more than five because such compounds may be purified by distillation. When the number of aryl groups is larger than five, alternative methods of purification, such as crystallization or column chromatography, may be required.

These polysilanes may be prepared by any synthetic method known in the art or to be developed; the method of synthesis is not critical. The aryl-substituted polysilanes are non-pyrophoric and are relatively insensitive to water, reacting slowly enough that they may come into contact with water for days without significant degradation. These partially arylated polysilanes may be purified by distillation, liquid column chromatography or crystallization techniques.

The second step of the method involves halogenation of the purified aryl-substituted polysilane to replace the aryl groups with halogen atoms and yield a partially halogenated polysilane. The method of halogenation is not critical and may be performed by reaction with HCl or HBr, for example. The halogenated polysilanes may also be purified by distillation, liquid column chromatography or crystallization techniques.

In a final step, the purified halogenated polysilanes are reduced directly or as complexes (see, for example, U.S. Pat. No. 5,942,637 of Boudjouk, which is herein incorporated by reference) to the corresponding trihydridosilyl-terminated polysilanes. The method of reduction is not critical and typical reaction conditions are well known in the art or may be determined by routine experimentation. Exemplary reducing agents which may be employed include lithium aluminum hydride, diisobutyl aluminum hydride, sodium aluminum hydride, and sodium aluminum hydride bis(methoxyethoxide). Alternatively, the halogenated polysilanes may be reduced indirectly through the corresponding alkoxylated polysilanes.

The method according to the invention is also applicable to the synthesis of trihydridosilyl-terminated perhydridooligosilanes, although these compounds are not the subject of the present application. These compounds, in which all of the silicon atoms are substituted with only hydrogen atoms, may be prepared by the conversion of triphenylsilyl-, diphenylhydrogensilyl- or phenyldihydrogensilyl-terminating groups to trihydridosilyl-terminal groups by dephenylation.

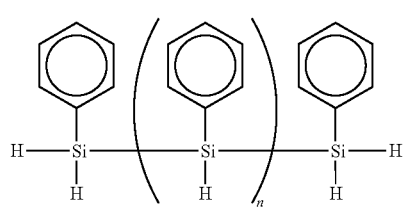

(5)

Oligophenylsilanes containing one phenyl and one hydrogen per internal silicon atom, as shown in formula (5), may be prepared by coupling phenylhydrogendichlorosilane with alkali metal or by the dehydrogenative coupling of phenylsilane by known methods (see, for example, Harrod, *J. Organometallic. Chem.*, 179: C11 (1985), Tilley, *Acc. Che. Res.*, 26: 22 (1993), and Marks, *Organometallics*, 10: 2543 (1991)) utilizing a variety of organometallic catalysts, typically consisting of Group IV or lanthanide metallocenes. These mixtures of oligomers can be separated into pure components by distillation. Using the general method described above, these compounds may then be converted to trihydridosilyl-terminated perhydridooligosilanes by dephenylation (halogenation followed by reduction).

If the oligophenylsilanes formed are cyclic, an additional step of ring opening by the addition of a halogen or cleavage of the ring with an alkali metal, followed by reaction with a halide or a triarylchlorosilane prior to purification or reduction, is required.

The utilization of perphenylpolysilanes for preparing perhydridopolysilanes is generally not practical since the purification of perphenylpolysilanes is difficult due to their high melting points and low volatility. Further, the molecular weight reduction forces high volume throughputs. For example, the simplest perphenyl compound with a silicon-silicon bond is hexaphenyldisilane, having a molecular weight of 518.8 Daltons and a melting point of 360-362° C. In contrast, the conversion compound is disilane with a molecular weight of only 58.2 Daltons, resulting in a dramatic molecular weight reduction. Accordingly, the method according to the invention is attractive and advantageous.

Coupling Method

A second method of the invention is used to prepare trihydridosilyl-terminated oligodimethylsilanes having formula (3) above. These oligosilanes contain at least four silicon atoms. Although there is no maximum number of silicon atoms which may be present in the oligodimethylsilane, preferred compounds contain no more than about ten silicon atoms due to volatility considerations in purification and CVD applications.

This method involves coupling a halogen-terminated oligosilane with an alkali metal salt of a mono-, di-, or triaryl silane to form a coupling product, halogenating the coupling product, and reducing the halogenated compound. These steps are described in more detail as follows.

In the first coupling step, a halogen (preferably chlorine or bromine)-terminated oligodimethylsilane is coupled with an alkali metal salt of a mono-, di-, or triaryl silane to form a mono-, di-, or trisilyl-terminated polydimethylsilane. The oligodimethylsilane preferably contains two to less than about eight silicon atoms so that the resulting coupling product will contain four to less than about ten silicon atoms. The oligodimethylsilane is preferably halogen-terminated at both termini.

Exemplary arylsilanes that may be used to form the alkali metal salts in the coupling reaction include triphenylchlorosilane, diphenylhydrogenchlorosilane, and phenyldihydrogenchlorosilane; analogous aryl silanes containing tolyl, anisyl, or other substituted phenyl groups may also be utilized. It is also within the scope of the invention to utilize metal salts of aryl-substituted higher silanes for coupling with the halogen-terminated oligosilane.

Although alternative alkali metals, such as sodium, may be employed, lithium is the preferred alkali metal for use in the coupling reaction. Sodium is typically less active than lithium, thus requiring harsher reaction conditions such as higher temperatures and pressure. Typical reaction conditions are well known in the art or may be determined by routine experimentation.

An exemplary coupling step utilizing lithium triphenylsilane and 1,2-dichlorotetramethyldisilane is illustrated in scheme (A) below. The coupling step results in the formation of a mono-, di-, or triarylsilyl terminated polydimethylsilane coupling product, which may be purified by recrystallization, for example. Exemplary coupling products containing triphenylsilyl-terminated polydimethylsilane and tritolylsilyl-terminated polydimethylsilane are shown in formulas (6) and (7).

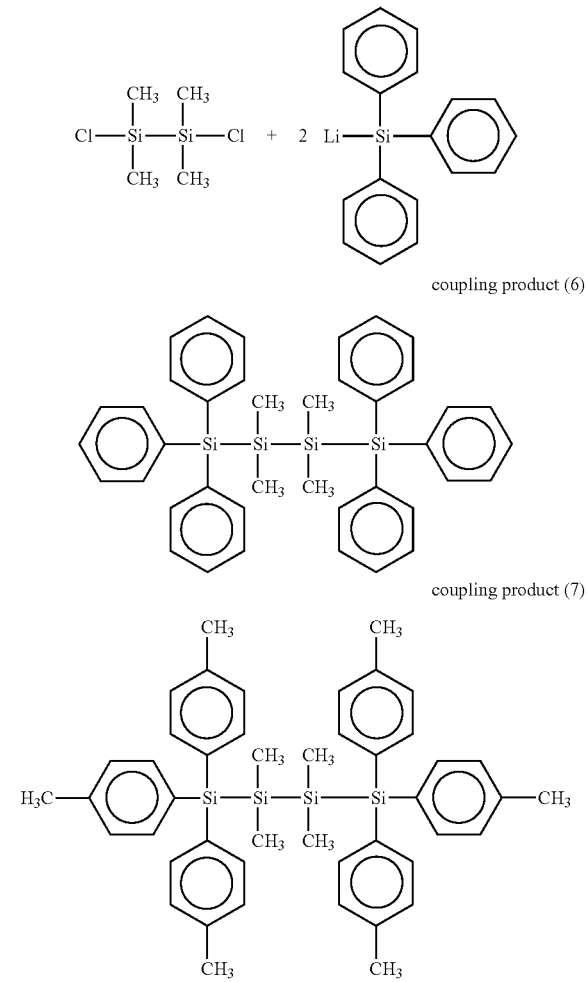

Scheme (A): coupling step coupling product (6)

coupling product (7)

In the second step of the method, the coupling product is halogenated with anhydrous hydrogen chloride or hydrogen bromide, preferably in the presence of a catalytic amount of a Lewis Acid (such as $AlCl_3$ or $FeCl_3$) to form a trichlorosilyl- or tribromosilyl-terminated polydimethylsilane intermediate, such as shown in formula (8). Although the use of HCl requires a Lewis Acid catalyst, reactions with HBr are facilitated by, but do not require, a Lewis Acid catalyst. This is an advantage over the HCl route, because paths for rearrangement catalyzed by Lewis Acids are mitigated. Typical reaction conditions are well known in the art or may be determined by routine experimentation.

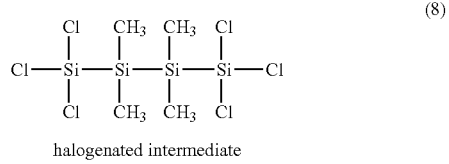

(8)

halogenated intermediate

Finally, the halogenated intermediate is reduced to the trihydridosilyl-terminated compound (such as shown in formula (9)) using lithium aluminum hydride, diisobutyl aluminum hydride, sodium aluminum hydride, or sodium aluminum hydride bis(methoxyethoxide)) or a similar metal hydride. Typical reaction conditions are well known in the art or may be determined by routine experimentation.

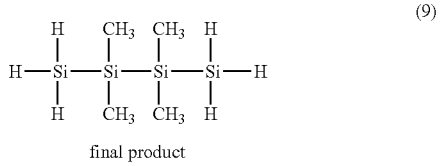

final product (9)

The methods according to the inventions are attractive because they provide the desired compounds in relatively high yields with minimal handling of pyrophoric intermediates and byproducts. This approach contrasts with known direct reduction of polysilanes at elevated temperature, in which an Si—Si bond is cleaved and converted to two Si—H bonds (see, for example, U.S. Pat. No. 4,079,071 of Neale). The prior art process does not generate trihydridosilyl terminations and does not allow for the preparation of pure oligosilanes.

EXAMPLES

The invention may be further understood in conjunction with the following, non-limiting examples.

Example 1

Preparation of 1,1,1,4,4,4-hexaphenyl-2,2,3,3-tetramethyltetrasilane Intermediate

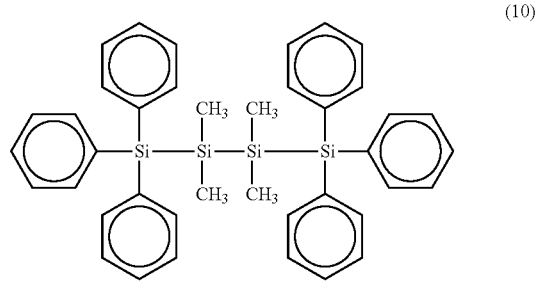

(10)

A 5 L, 4-neck flask equipped with a cooling bath, a magnetic stirrer, a pot thermometer, an addition funnel, and a nitrogen protected dry-ice condenser was charged with 1000 ml of dry tetrahydrofuran followed by 27.8 g of cut lithium ribbon. With mechanical stirring, a solution of 589.7 g of triphenylchlorosilane dissolved in 1000 ml of tetrahydrofuran was added to the flask while maintaining pot temperature at 0° to 20° C. Once the addition was complete, the mixture was stirred for 10 hours until all of the lithium metal was consumed, forming a mixture containing triphenylsilyl lithium. Another similar 5 L flask was charged with 187.2 g of 1,2-dichlorotetramethyldisilane and 200 ml of tetrahydrofuran and then cooled to 0° C. The triphenylsilyl lithium mixture was added while maintaining temperature at 0°-10° C. and then stirred for 4 hours.

The mixture was then heated to 60-80° C. for 26 hours. The addition funnel and condenser were replaced by a distillation head, and approximately 1.5 L of tetrahydrofuran was removed. The mixture was cooled to room temperature. The distillation head was removed, and the addition funnel and condenser were remounted on the flask. 500 ml of hexane were added, followed by the slow addition of 1000 ml of water, and then the mixture was stirred for 15 minutes.

The mixture was filtered on a Buchner funnel. The solids were suspended in 500 ml of water and then separated by filtration again. The solids were washed twice with 800 ml volumes of hexane and then dried in an oven at 80° C. for 4 hours. A total of 410 g of 1,1,1,4,4,4-hexaphenyl-2,2,3,3-tetramethyltetrasilane product (formula (10)) was obtained. Trace amounts of water in the product could be removed by Dean-Stark azeotropic distillation by dissolving 100 g of the product in 1 L of toluene.

Example 2

Preparation of 1,1,1,4,4,4-hexachloro-2,2,3,3-tetramethyltetrasilane Intermediate

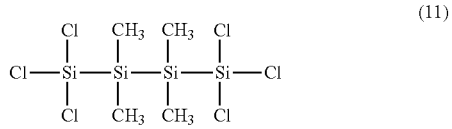

(11)

A 5 L, 4-neck flask equipped with a pot thermometer, a gas sparge tube and a nitrogen protected dry-ice condenser was charged with 3000 ml of dry toluene, 406.5 g of 1,1,1,4,4,4-hexaphenyl-2,2,3,3-tetramethyltetrasilane (prepared in Example 1) and 20.3 g of anhydrous aluminum chloride. The mixture was then heated to approximately 30° C., and a slow sparge of anhydrous hydrogen chloride was commenced. The pot temperature rose to 60° over an hour and then began to drop. Hydrogen chloride sparge was halted. A small sample of the mixture was taken and volatiles stripped under vacuum. $^1$H NMR indicated that no aromatic protons were present.

A nitrogen sparge was then utilized to remove excess hydrogen chloride. The gas sparge tube and the condenser were removed from the flask and a distillation head was mounted. Volatile components were removed at 1 mm Hg at a maximum pot temperature of 40° C. The mixture was allowed to cool to room temperature and 500 ml of hexane were added and stirred for 15 min. The salts were removed by filtration. The salts were washed with 100 ml of hexane and added to the filtrate. The filtrate was stripped of all volatiles at 30-40° C. for 2 hours at 1 mm Hg. The pot showed a single $^1$HNMR peak at 0.55 ppm. GC in hexane indicated 94.6% purity of 1,1,1,4,4,4-hexachloro-2,2,3,3-tetramethyltetrasilane (formula 11)). The overall yield of the product was 191 g (77%). The product had an observed mp of 16-18° C.

Example 3

Preparation of 2,2,3,3-tetramethyltetrasilane

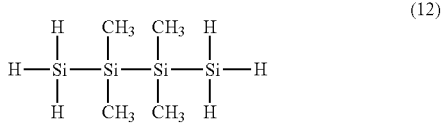

(12)

A 1 L, 3-neck flask equipped with a cooling bath, a magnetic stirrer, a pot thermometer, an addition funnel, and a nitrogen protected dry-ice condenser was charged with 38.5 g (0.1 mol) of 1,1,1,4,4,4-hexachloro-2,2,3,3-tetramethyldisilane (prepared in Example 2) dissolved in 50 ml of ether and cooled to −10° to 5° C. Separately, 6.5 g of lithium aluminum hydride was combined with 400 ml of dry ether. This mixture was stirred at 35°-40° C. until the lithium aluminum hydride was well-dispersed and then allowed to cool to room temperature. The mixture was transferred to an addition funnel mounted on the 1 L flask and then added over a period of thirty minutes while maintaining the pot temperature below 5° C. The pot temperature was allowed to return to 0° C. after the addition was complete. Volatile components were flash distilled through a Vigreux column with a dry-ice distillation head with a vacuum of 2-3 mm Hg at 0° C. The volatiles were redistilled through a Vigreux column. 7.4 g (yield: 60%) of clear liquid were collected at 20-4° C. at 1 mm Hg: GC indicated>90% purity. IR and $^1$H NMR results were consistent with the target structure, 2,2,3,3-tetramethyltetrasilane (formula (12)).

Example 4

Preparation of Bromine-Terminated Oligodimethylsilane Intermediates

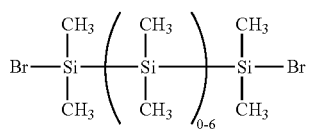

(13)

A 2 L, 4-neck flask equipped with a cooling bath, a mechanical stirrer, a pot thermometer, an addition funnel, and a nitrogen protected condenser was charged with 500 ml of methylene chloride and 200 g of polydimethylsilane (molecular weight 1000-3000). With agitation, 183.7 g of bromine was slowly added to the mixture while maintaining the temperature at 30-40° C. The addition rate was controlled by observing the disappearance of orange-red color as the bromine was consumed. The mixture was filtered to remove solids. The solids were not analyzed but assumed to be either unreacted polydimethylsilane or bromine terminated polydimethylsilane. The filtrate was transferred to a 2 L flask equipped with a short distillation column. The mixture was stripped at atmospheric pressure to a pot temperature of 70° C. The pressure was reduced to 30 mm Hg. A volatile fraction of dimethyldibromosilane was removed. A fraction having a boiling point of 79° C./30 mm that solidified during storage was identified as 1,2-dibromotetramethyldisilane by GC/MS. A fraction having a boiling point of 100-110° C./10 mm with a density (25° C.) of 1.247 was identified as 1,3-dibromohexamethyltrisilane. The pot contained mixed bromine terminated oligomers with 4 or more silicon atoms, as shown in formula (13). The density (25° C.) of the red fluid was 1.213.

Using a similar synthetic method, bromine terminated polyphenylmethylsilane may be prepared via the reaction of bromine with polyphenylmethylsilane in place of polydimethylsilane.

Bromine-terminated oligodimethylsilanes may be used as intermediates in the preparation of trihydridosilyl-terminated polysilanes by direct reduction. Alternatively, higher bromine terminated polydimethylsilane homologs may also be converted to trihydridosilyl terminated polydimethylsilanes by successive reaction with triphenylsilyl lithium to yield an aryl-substituted polysilane (as described in Example 1), dephenylation with hydrogen chloride or hydrogen bromide (as described in Example 2), and reduction (as described in Example 3).

Example 5

Preparation of 2,2,3,3,4,4-hexamethylpentasilane 2,2,3,3,4,4-hexamethylpentasilane was prepared from dibromohexamethyltrisilane (prepared in Example 4) by coupling, halogenation and reduction steps analogous to the methods described in Examples 1, 2 and 3, respectively. The product had a boiling point of 110-115° C./0.15 mm, and the structure of the product was confirmed with NMR.

Example 6

Preparation of 1,2,3-triphenyltrisilane and 1,2,3,4-tetraphenyltetrasilane

A 50 ml reaction flask equipped with magnetic stirrer, pot thermometer, condenser septum, and cooling bath was charged with 5.0 g of bis(diphenylphoshine)propanenickel (II) chloride and 40 ml of diethyl ether, then cooled to −20° C. Methyl lithium (0.019 moles of 1.6 M in ether) was added by syringe, maintaining the temperature below −10° C. After complete addition of methyl lithium, the mixture was stirred for one hour at 0° C. The red-brown organonickel complex formed a solution, with lithium chloride precipitating out as a yellow suspension.

A separate 500 ml reaction flask equipped with magnetic stirrer, pot thermometer, condenser septum, and cooling bath was charged with 100 g of phenylsilane. While maintaining temperature at 20-40° C., the organonickel catalyst was added in four portions over 60 minutes. An exotherm and gas evolution were observed. The reaction mixture was stirred at room temperature for 4 hours and then at 40° for 6 hours.

The major product isolated was 1,2,3-triphenyltrisilane (bp 85° C./0.001 mm). The minor product was 1,2,3,4-tetraphenyltetrasilane and its branched isomer. These products were not pyrophoric and could be separated by conventional or wiped film distillation.

Example 7

Preparation of 1,2,3-trichlorotrisilane

A 1 L, 3-neck flask equipped with a cooling bath, a magnetic stirrer, a pot thermometer, an addition funnel, and a nitrogen bubbler protected condenser was charged with 2 g of aluminum chloride and 200 ml of xylene. 50 ml of xylene was distilled off in order to remove any trace water. The mixture was cooled to −20° C., and 40 g triphenyltrisilane (prepared in Example 6) was added. Through a gas frit, 59.2 g of anhydrous hydrogen chloride was added over one hour at a rate so that gas did not exit the bubbler, and temperature was maintained below 35° C. As the reaction neared completion, the rate of HCl consumption dropped to almost zero and the temperature fell. After the reaction was complete, the pot was sparged with nitrogen to remove any unreacted HCl. The product was identified by GC/MS as 1,2,3-trichlorotrisilane. This product was not pyrophoric and could be purified by conventional or wiped film distillation.

Example 8

Preparation of Tetrasilane 1,2,3,4-Tetraphenyltetrasilane intermediate prepared in Example 6 may be converted to 1,2,3,4-tetrachlorotetrasilane, as described in Example 2. The chlorinated intermediate may then be reduced to tetrasilane as described in Example 3.

Example 9

Preparation of Tris(trichlorosilyl)silane

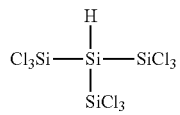

(14)

A 5 L, 4-neck flask equipped with a mechanical stirrer, pot thermometer, an addition funnel, and a nitrogen protected dry-ice condenser was charged with 1500 ml of tetrachlorosilane (utilized as a solvent) and 1132.0 g of perchloroneopentasilane. The mixture was then heated to 40-50° C. and stirred until the perchloroneopentasilane dissolved. The mixture was allowed to return to room temperature. The formation of solids was observed, but did not interfere with smooth agitation. A 0.5 molar equivalent of a solution of 2M HCl in ether was added over 2 hours, while maintaining pot temperature of 15-25° C. A sample of the mixture was analyzed by GC/MS to confirm formation of the product. A second 0.5 molar equivalent of a solution of 2M HCl in ether was again added over 2 hours, while maintaining pot temperature of 15-25° C., during which time the reaction mixture became a clear solution.

The mixture was purified by distillation. Silicon tetrachloride was removed at atmospheric pressure without allowing pot temperature to exceed 80° C. The product, tris(trichlorosilyl)silane, was distilled at 60-62° C./0.2 mm Hg and recovered at 70% yield. The tris(trichlorosilyl)silane product (formula (14)), identified by GC/MS, had a melting point of 31° C. and a density (25° C.) of 1.539.

Example 10

Preparation of 2-(2-Ferrocenylethenyl)isotetrasilane

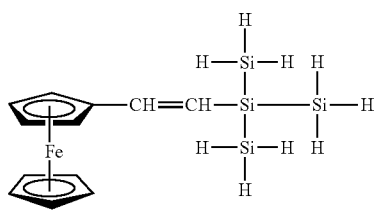

(15)

Tris(trichlorosilyl)silane prepared in Example 9 is dissolved in toluene with a molar equivalent of vinylferrocene and tris(triphenylphoshine)rhodium chloride (Wilkinson's catalyst) and heated for >4 hours to form tris(trichlorosilyl)silylvinylferrocene by dehydrogenative coupling. This intermediate can be reduced to form 2-(2-ferrocenylethenyl)isotetrasilane (formula (15)), as described in Example 3.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A trihydridosilyl-terminated polysilane having formula (1), comprising at least four silicon atoms and at least one silicon terminus bonded to three hydrogen atoms,

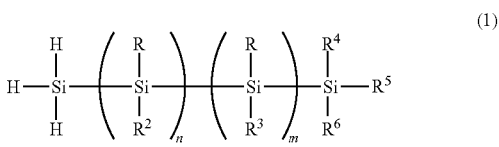

(1)

wherein R represents an organic substituent, $R^2$ and $R^3$ are not identical and are independently selected from the group consisting of an organic substituent, a hydrogen, and a substituted silyl group, $R^4$, $R^5$, and $R^6$ are independently selected from the group consisting of an organic substituent, a substituted silicon atom and hydrogen, and m and n are each independently integers selected so that the total number of silicon atoms is at least 4.

2. The trihydridosilyl-terminated polysilane according to claim 1, wherein the number of silicon atoms is not more than about 10.

3. The trihydridosilyl-terminated polysilane according to claim 1, wherein $R^4$, $R^5$, and $R^6$ are hydrogen.

4. The trihydridosilyl-terminated polysilane according to claim 3, wherein $R=R^2=CH_3$, n=2, and m=0.

5. The trihydridosilyl-terminated polysilane according to claim 3, wherein $R=R^2=CH_3$, n is an integer of about 3 to 8, and m=0.

6. The trihydridosilyl-terminated polysilane according to claim 3, wherein n=1, m=0, $R=SiH_3$, and $R^2$=2-ferrocenylethenyl.

7. A method for preparing a trihydridosilyl-terminated polysilane comprising:
   (a) preparing a non-pyrophoric aryl-substituted polysilane comprising at least four silicon atoms and an aryl-substituted silicon terminus;
   (b) halogenating the aryl-substituted polysilane to produce a halogenated polysilane; and
   (c) reducing the halogenated polysilane to yield a trihydridosilyl-terminated polysilane.

8. The method according to claim 7, wherein the aryl-substituted silicon terminus comprises between one and three aryl substituents.

9. The method according to claim 7, wherein the aryl substituents are selected from the group consisting of phenyl, tolyl, and anisyl.

10. The method according to claim 7, further comprising purifying the aryl-substituted polysilane by a method selected from the group consisting of distillation, liquid chromatography, and crystallization.

11. The method according to claim 7, further comprising purifying the halogenated polysilane by a method selected from the group consisting of distillation, liquid chromatography, and crystallization.

12. The method according to claim 7, wherein the trihydridosilyl-terminated polysilane comprises not more than about 10 silicon atoms.

13. The method according to claim 7, wherein the trihydrido-terminated polysilane is a trihydrido-terminated perhydridopolysilane.

14. The method according to claim 7, wherein the trihydrido-terminated polysilane has formula (1):

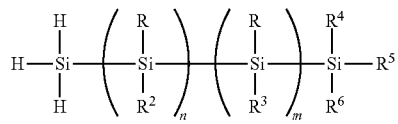

(1)

wherein R represents an organic substituent, $R^2$ and $R^3$ are not identical and are independently selected from the group consisting of an organic substituent, a hydrogen, and a substituted silyl group, $R^4$, $R^5$, and $R^6$ are independently selected from the group consisting of an organic substituent, a substituted silicon atom and hydrogen, and m and n are each independently integers selected so that the total number of silicon atoms is at least 4.

15. A method for preparing a trihydridosilyl-terminated oligodimethylsilane comprising:
    (a) coupling a halogen-terminated oligosilane with an alkali metal salt of a mono-, di-, or tri-aryl silane to form a coupling product;
    (b) halogenating the coupling product to form a halogenated intermediate; and
    (c) reducing the halogenated intermediate to form a trihydridosilyl-terminated oligodimethylsilane.

16. The method according to claim 15, wherein the alkali metal comprises lithium.

17. The method according to claim 15, wherein the arylsilane is selected from the group consisting of a triarylchlorosilane, a diarylhydrogenchlorosilane, and an aryldihydrogenchlorosilane.

18. The method according to claim 15, wherein the aryl group is selected from the group consisting of phenyl, tolyl, and anisyl.

19. The method according to claim 15, wherein step (b) is performed using HCl or HBr in the presence of a Lewis Acid.

20. The method according to claim 15, wherein the trihydridosilyl-terminated oligodimethylsilane has formula (3), wherein n is an integer greater than 2:

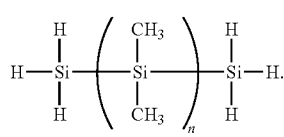

(3)

* * * * *